United States Patent
Hsieh et al.

(10) Patent No.: US 7,215,734 B2
(45) Date of Patent: May 8, 2007

(54) METHOD AND SYSTEM FOR THREE-DIMENSIONAL RECONSTRUCTION OF IMAGES

(75) Inventors: Jiang Hsieh, Brookfield, WI (US); Xiangyang Tang, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 379 days.

(21) Appl. No.: 10/881,794

(22) Filed: Jun. 30, 2004

(65) Prior Publication Data

US 2006/0002507 A1    Jan. 5, 2006

(51) Int. Cl.
    *A61B 6/03* (2006.01)
(52) U.S. Cl. ............... 378/19; 378/4; 378/15
(58) Field of Classification Search ............ 378/4, 378/15, 19
    See application file for complete search history.

(56) References Cited

U.S. PATENT DOCUMENTS

| | | | |
|---|---|---|---|
| 4,136,388 A | 1/1979 | Lindquist | |
| 4,205,375 A | 5/1980 | Inouye et al. | |
| 4,852,132 A | 7/1989 | Namikawa | |
| 5,400,379 A | 3/1995 | Pfoh et al. | |
| 5,577,501 A | 11/1996 | Flohr et al. | |
| 5,712,895 A | 1/1998 | Negrelli et al. | |
| 5,825,842 A * | 10/1998 | Taguchi | 378/15 |
| 5,907,592 A | 5/1999 | Levinson | |
| 5,907,594 A | 5/1999 | Lai | |
| 5,960,056 A | 9/1999 | Lai | |
| 5,974,108 A | 10/1999 | Taguchi et al. | |
| 5,987,091 A | 11/1999 | Miyazaki et al. | |
| 5,987,157 A | 11/1999 | Schaller et al. | |
| 6,115,445 A | 9/2000 | Lai | |
| 6,178,220 B1 | 1/2001 | Freundlich et al. | |
| 6,201,849 B1 | 3/2001 | Lai | |
| 6,256,366 B1 | 7/2001 | Lai | |
| 6,381,487 B1 * | 4/2002 | Flohr et al. | 600/425 |
| 6,389,097 B1 | 5/2002 | Bulkes et al. | |
| 6,529,576 B2 | 3/2003 | Hsieh et al. | |
| 6,574,298 B2 | 6/2003 | Heuscher | |
| 6,771,732 B2 | 8/2004 | Xiao et al. | |
| 6,775,346 B2 | 8/2004 | Heuscher et al. | |
| 6,917,663 B2 * | 7/2005 | Taguchi et al. | 378/8 |
| 7,062,009 B2 * | 6/2006 | Karimi et al. | 378/19 |

* cited by examiner

*Primary Examiner*—Edward J. Glick
*Assistant Examiner*—John M. Corbett
(74) *Attorney, Agent, or Firm*—The Small Patent Law Group; Dean D. Small

(57) ABSTRACT

A method and system for three-dimensional reconstruction of images are provided. The method includes receiving projection data from an imaging device scanning an object, identifying projection data corresponding to a conjugate pair of projection rays, and interpolating the projection data corresponding to the conjugate pair of projection rays to reconstruct an image of the object being scanned.

17 Claims, 3 Drawing Sheets

METHOD AND SYSTEM FOR THREE-DIMENSIONAL RECONSTRUCTION OF IMAGES

BACKGROUND OF THE INVENTION

This invention relates generally to image reconstruction, and more particularly, to methods and systems for reconstruction of volumetric computed topography (CT) images.

Three-dimensional (3D) or cone beam (CB) filtered backprojection (FBP) is used in multi-row CT scanners to provide volumetric CT (VCT) scanning operation. It is known to use 3D backprojection algorithms in VCT scanners to reconstruct images using a mapping process. For example, 3D FBP may be used for image reconstruction from cone beam projections acquired from a circular source trajectory. Using a pixel based backprojection, a mapping process is typically performed from the center of a reconstructed pixel to a detector plane. However, in many instances it is unlikely that the reconstruction point is at the center of a detector row. As a result, interpolation is performed across rows of the detector. For example, a backprojected value is determined, which is the weighted sum of several filtered projection samples (e.g., four filtered projection samples from four adjacent detector elements).

Thus, known backprojection processes performing interpolation use several detector elements, which may be from adjacent rows of the detector, to calculate a back-projected value from an intersecting location. An estimated value is thereby used for reconstructing images. This process results in a larger reconstructed image slice thickness, thereby reducing spatial resolution.

BRIEF DESCRIPTION OF THE INVENTION

In one exemplary embodiment, a method for reconstructing an image of an object is provided. The method includes receiving projection data from an imaging device scanning an object, identifying projection data corresponding to a conjugate pair of projection rays, and interpolating the projection data corresponding to the conjugate pair of projection rays to reconstruct an image of the object being scanned.

In another exemplary embodiment, a computed tomography (CT) imaging device having a multi-row detector is provided and configured to acquire projection data from a scan of an object, identify projection data corresponding to a conjugate pair of projection rays and interpolate the projection data corresponding to the conjugate pair of projection rays to reconstruct an image of the object being scanned.

DETAILED DESCRIPTION OF THE INVENTION

Figure 1:
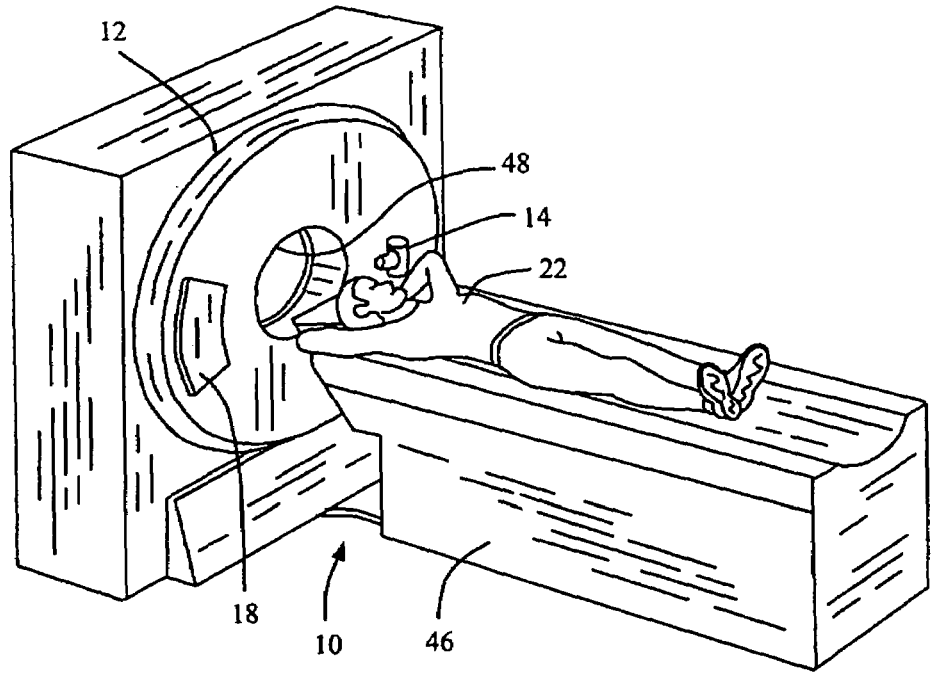
FIG. 1 is a pictorial view representative of a CT imaging device in accordance with various embodiments of the invention.

Various exemplary embodiments of systems and methods for reconstructing images of an object are described below in detail. Technical effects of the systems and methods described herein include using multiple projection beams during interpolation to provide an improved slice-sensitivity-profile (SSP) for image reconstruction of actual images of an object.

In some known CT imaging system configurations, an X-ray source projects a fan-shaped beam that is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements (i.e., projection data) from the detector array at one gantry angle is referred to as a "view". A "scan" of the object comprises a set of views made at different gantry angles, or view angles, during one revolution of the X-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle, detector row index, and detector channel index. Specifically, prior to a filtered backprojection process, the data is weighted according to a helical weighing factor, which is a function of the gantry angle, detector row, and detector angle. The weighted projection is then filtered and backprojected to construct an image that corresponds to a two-dimensional slice taken through the object.

To further reduce the total acquisition time, multi-slice CT has been introduced. In multi-slice CT, multiple rows of projection data are acquired simultaneously at one time. When combined with helical scan mode, the system generates a single helix of cone beam projection data. Similar to the single slice helical weighting scheme, a method can be derived to multiply the weight with the projection data prior to the filtered backprojection algorithm.

As used herein, an element or step recited in the singular and proceeded with the word "a" or "an" should be understood as not excluding plural elements or steps, unless such exclusion is explicitly recited. Furthermore, references to "one embodiment" or "an embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated, but a viewable image is not. However, many embodiments generate (or are configured to generate) at least one viewable image.

Figure 2:
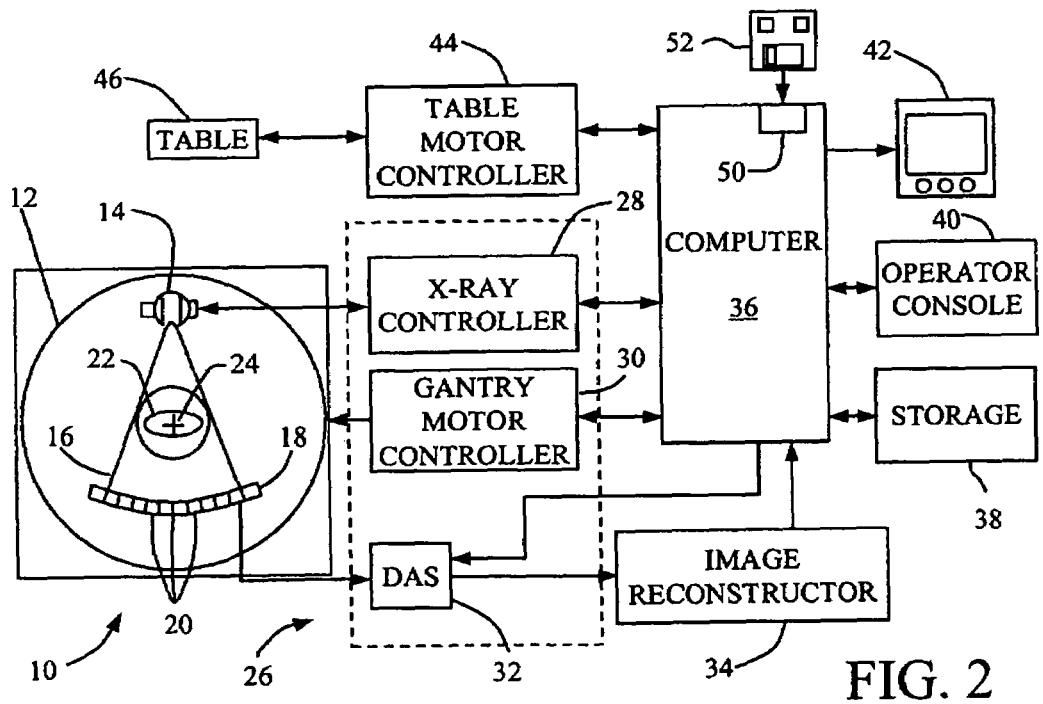
FIG. 2 is a functional block diagram of the CT imaging device illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an X-ray tube 14 (also called X-ray source 14 herein) that projects a beam of X-rays 16 toward a detector array 18 on the opposite side of gantry 12. Detector array 18 is formed by a plurality of detector rows (not shown) including a plurality of detector elements 20 which together sense the projected X-rays that pass through an object, such as a medical patient 22 between array 18 and source 14. Each detector element 20 produces an electrical signal that represents the intensity of an impinging X-ray beam and hence can be used to estimate the attenuation of the beam as it passes through object or patient 22. During a scan to acquire X-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of X-ray source 14 are governed by a control mechanism 26 of CT imaging system 10. Control mechanism 26 includes an X-ray controller 28 that provides power and timing signals to X-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 (or any other suitable display device) allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes an instruction-obtaining device 50, for example, a floppy disk drive, CD-ROM drive, DVD drive, magnetic optical disk (MOD) device, or any other digital device including a network connecting device such as an Ethernet device. Instruction-obtaining device 50 is provided to read instructions and/or data from a computer-usable medium 52, such as a floppy disk, a CD-ROM, or a DVD having a computer readable program embodied thereon. The program, in some embodiments is configured to instruct a computer, e.g., computer 36, to perform functions described herein and/or send signals to other devices to perform some or all of the functions. In some embodiments, instruction-obtaining device 50 obtains program instructions from another digital source such as a network or the Internet, or yet to be developed digital means. In another embodiment, computer 36 executes instructions stored in firmware (not shown). Computer 36 is programmed to perform functions described herein and/or send signals to other devices to perform some or all of the functions. As used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating X-ray source) and fifth generation CT systems (stationary detector and X-ray source). Additionally, it is contemplated that the benefits of the various embodiments of the invention accrue to imaging modalities other than CT. Additionally, although the herein described methods and systems are described in a medical setting, it is contemplated that the benefits of the various embodiments of the invention accrue to non-medical imaging systems such as those systems typically employed in an industrial setting or a transportation setting, such as, for example, but not limited to, a baggage scanning system for an airport or other transportation center.

Figure 3:
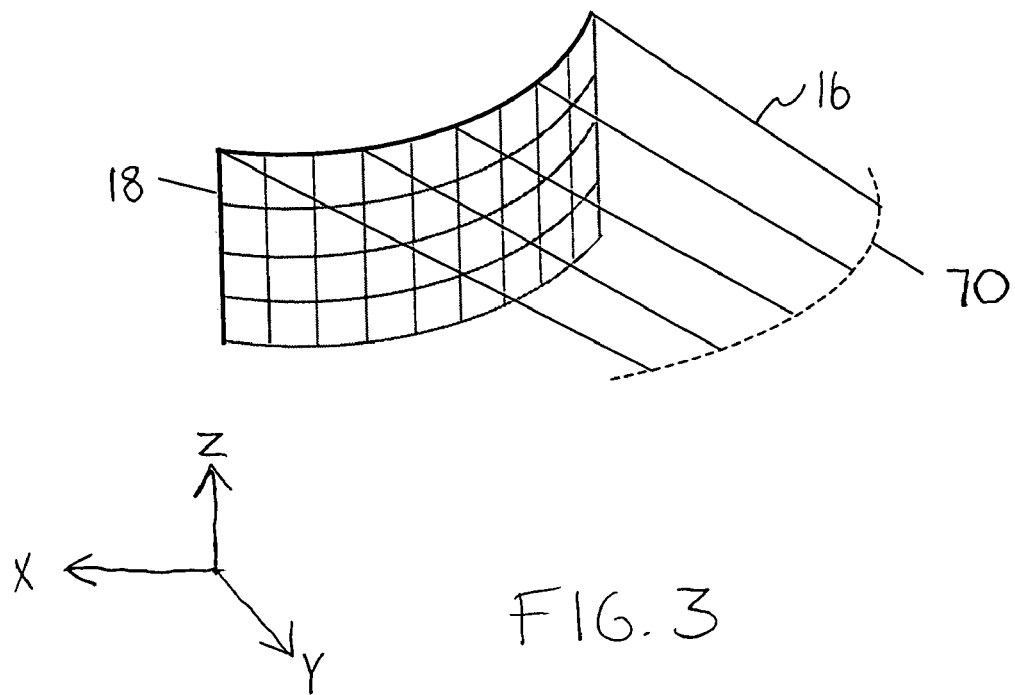
FIG. 3 is a diagram illustrating a cone-parallel rebinning geometry.

When CT imaging system 10 is used as a volumetric CT scanner, the perspective geometry of the helical source trajectory and projection data acquisition in a volumetric CT scanner is shown in FIG. 3, where (x, y, z) represents the local coordinate system for a cylindrical multi-row CT detector array 18. Specifically, during the reconstruction process using the CT imaging system 10, a cone beam to parallel beam rebinning as is known is first performed. After the rebinning process, the original cone beam sampling is converted into a tilted parallel geometry as shown in FIG. 3. It should be noted that in this configuration, all samples in a single view have the same projection angle, although they may have different tilt angles. Thus, a cone-parallel rebinning geometry for a source trajectory 70 (shown as a dotted line) is provided as shown is FIG. 3.

Figure 4:
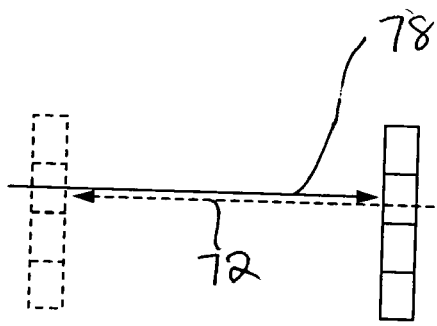
FIG. 4 is a diagram illustrating conjugate samples of non-tilted parallel rays.
Figure 5:
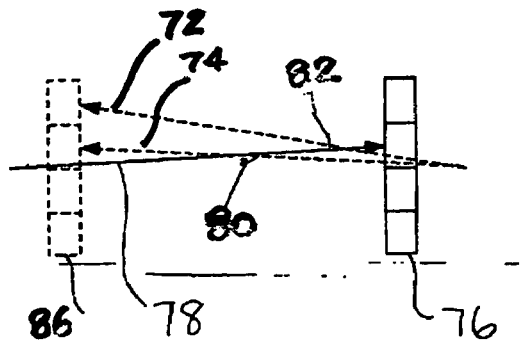
FIG. 5 is a diagram illustrating conjugate samples of tilted parallel rays.

As a result of the rebinning process, each sample in a projection corresponds to a conjugate sample in another projection. This is due to all the samples in the same view having the same view angle. Thus, for two views that are 180° apart, referred to herein as a conjugate pair, each sampling pair corresponds to the same projection or ray path if the difference in z is not considered. It should be noted that in the non-tilted case, as shown in FIG. 4, two samples of non-tilted parallel projections or rays 72 form a conjugate sample for every reconstruction location along a horizontal line. In the tilted cone beam case, as shown in FIG. 5, the conjugate sampling pair defined by tilted projections changes with the reconstruction pixel location. Specifically, in FIG. 5, the solid line represent the current view-of-interests. In particular, detector 76 represents the detector position at this view-of-interest and ray 80 represents one of the backprojection rays for the same view. The dotted lines represent the conjugate view-of-interests. These conjugate views are 180-degrees apart from the view-of-interest. Detector 86 and rays 72 and 74 illustrate the detector position and two of the backprojection rays for the conjugate view. It should be noted that for each reconstruction pixel, there is a unique pair of conjugate samples. For example, for reconstruction pixel 80, the pair of rays that intersect this location are rays 78 and 74. The pair of rays for reconstruction pixel 82 are rays 78 and 72.

Figure 6:
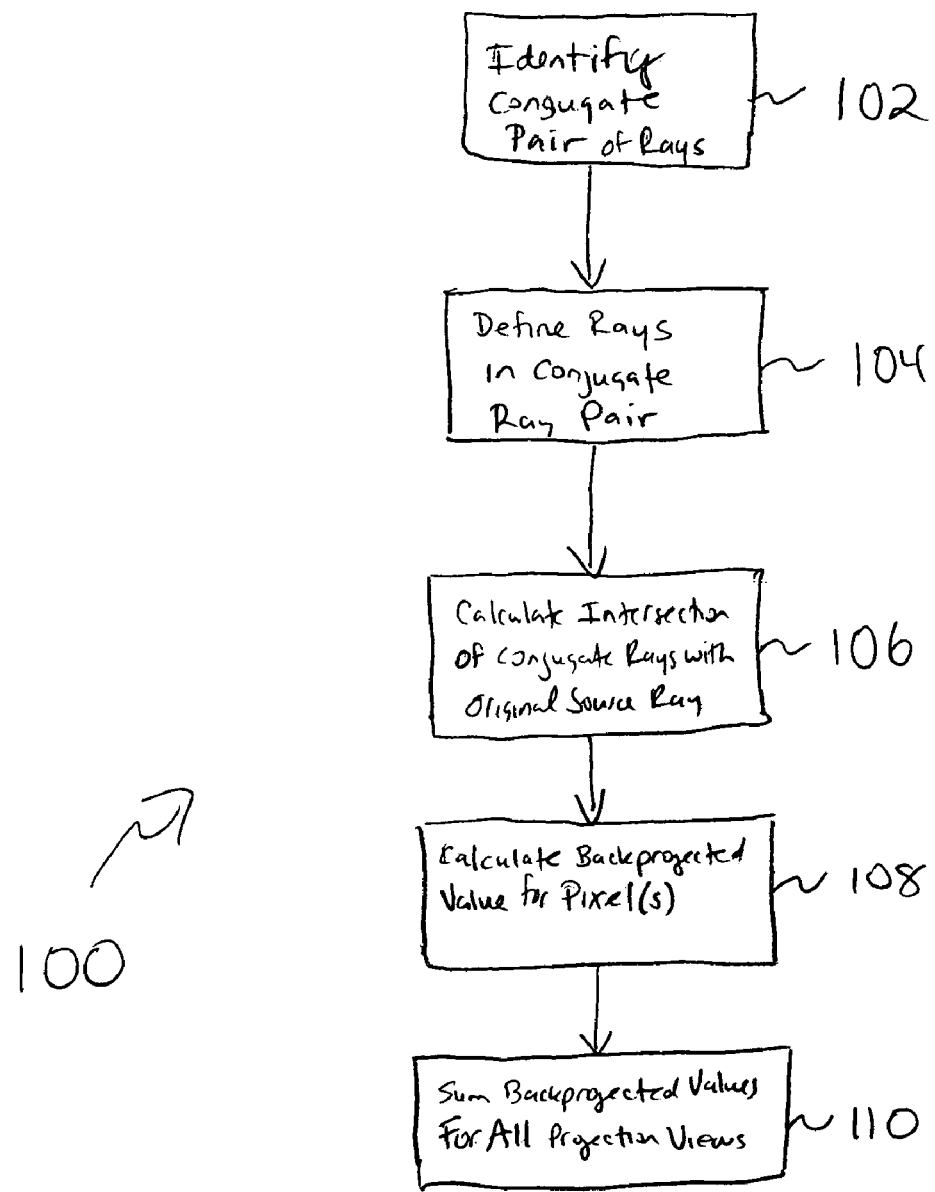
FIG. 6 is a flowchart of a backprojection process in accordance with an exemplary embodiment of the invention.

Various embodiments of the invention provide a backprojection process 100 as shown in FIG. 6. As shown therein, at 102 conjugate samples are identified on a pixel-by-pixel basis. Specifically, two of the projections or rays (e.g., ray pairs 74 defined by projected X-rays as shown in FIG. 5) that are 180° apart (i.e., a conjugate pair) are identified and examined at the same time to obtain projection data corresponding thereto. More particularly, two intersections are calculated. The first is the same as a conventional backprojection. The second is the intersection of the ray that passes the same reconstruction pixel (and the corresponding source position) with the detector at the projection angle that is 180-degrees apart from the current view. The final interpolation is performed using projection samples from both views. The selection of the samples and the interpolation coefficients as described in more detail below.

Thereafter at 104, the projections or rays in the conjugate pair are defined. Specifically, $p(\gamma, \beta, q)$ and $p(-\gamma, \beta+\pi, q')$ denote the projection samples corresponding to two rays, for example, two rays that form the ray pair 78 and 74 (shown in FIG. 5) that pass through the reconstructed pixel (x, y, z) and intersect two detector elements 76 and 86 (shown in FIG. 5). It should be noted that the projection angle of the two rays differ by 180-degrees. It should be noted that q defines a detector row, for example, in the detector array 18 (shown in FIG. 3) not the absolute distance, for example, in millimeters (mm), $\gamma$ defines a detector angle and $\beta$ defines a projection angle. Further, i and i' denote the integer part of the q and q' and $\Delta$ and $\Delta'$ denote the fraction part of the q and q', respectively. It should be noted that the value of q is larger than zero.

For exemplary purposes only, the backprojection of reconstruction pixel 80 (shown in FIG. 5) will now be described. However, it should be noted that this process applies to any pixel. At 106, the intersections are calculated. Specifically, the intersection of the ray 78 (shown in FIG. 5) (that intersects reconstruction pixel 80) with the detector 76 is calculated based on a known source and detector position (e.g., as shown in FIG. 3). Next, the intersection of ray 74 (intersecting the same reconstruction pixel 80) with the detector 86 is calculated. Essentially, for each voxel position, two intersection points are calculated. In particular, a fraction part ($\Delta$ and $\Delta'$) and an integer part (i and i') are calculated for both the ray 78 and the conjugate ray 78. Specifically, at 108 the backprojected value for the pixel (x, y, z) is calculated by the following equations:

$$\begin{cases} \frac{1-\Delta'}{1-\Delta'+\Delta} p(\gamma, \beta, i) + \frac{\Delta}{1-\Delta'+\Delta} p(-\gamma, \beta+\pi, i'+1), & \Delta \leq \Delta' \quad (1) \\ \frac{\Delta}{1-\Delta'+\Delta} p(\gamma, \beta, i+1) + \frac{1-\Delta'}{1-\Delta'+\Delta} p(-\gamma, \beta+\pi, i'), & \Delta > \Delta' \quad (2) \end{cases}$$

It should be noted that although linear interpolation is used, the various embodiments are not so limited. For example, Lagrange and other forms of interpolation may be implemented as desired or needed.

Then, at 110, the backprojected values are accumulated or summed for all projection views to formulate the final intensity of the reconstructed image.

Various embodiments of the invention provide interpolation for backprojection image processing using two projections or rays, and more particularly, a conjugate ray pair. The various embodiments provide an improved slice-sensitivity-profile (SSP) without introducing additional artifacts.

While the invention has been described in terms of various specific embodiments, those skilled in the art will recognize that the invention can be practiced with modification within the spirit and scope of the claims.

What is claimed is:

1. A method for reconstructing an image of an object, said method comprising:
    receiving projection data from an imaging device scanning an object;
    identifying projection data corresponding to a conjugate pair of projection rays;
    determining an integer part and a fraction part for the projection data corresponding to each projection ray in the conjugate pair and for a source projection ray;
    interpolating the projection data corresponding to the conjugate pair of projection rays to reconstruct an image of the object being scanned based on a comparison of the fractional parts of the conjugate rays; and
    displaying the reconstructed image.

2. A method in accordance with claim 1 wherein the imaging device is a computed tomography imaging device.

3. A method in accordance with claim 1 wherein the conjugate pair is defined by two projection rays spaced 180 degrees apart relative to projection angle.

4. A method in accordance with claim 1 wherein identifying projection data corresponding to a conjugate pair comprises determining projection data on a pixel-by-pixel basis.

5. A method in accordance with claim 1 wherein the interpolating comprises performing calculations in accordance with:

$$\begin{cases} \frac{1-\Delta'}{1-\Delta'+\Delta} p(\gamma, \beta, i) + \frac{\Delta}{1-\Delta'+\Delta} p(-\gamma, \beta+\pi, i'+1), & \Delta \leq \Delta' \quad (1) \\ \frac{\Delta}{1-\Delta'+\Delta} p(\gamma, \beta, i+1) + \frac{1-\Delta'}{1-\Delta'+\Delta} p(-\gamma, \beta+\pi, i'), & \Delta > \Delta' \quad (2) \end{cases}$$

wherein q defines a detector row, $\gamma$ defines a detector angle, $\beta$ defines a projection angle, i and i' denote the integer part of q and q' and $\Delta$ and $\Delta'$ denote the fraction part of q and q'.

6. A method in accordance with claim 1 wherein the reconstruction is performed on a pixel-by-pixel basis and further comprising determining two intersecting points for each reconstruction voxel.

7. A method in accordance with claim 1 wherein the interpolating is performed for each of the projection rays in the conjugate pair.

8. A method in accordance with claim 1 wherein the interpolating comprises a linear interpolation.

9. A method in accordance with claim 1 wherein identifying projection data comprises determining a source and detector position for the imaging device for each conjugate pair of projection rays.

10. A method for providing backprojection image reconstruction, said method comprising:
   determining projection data from an imaging device corresponding to a conjugate pair of projection rays, the projection data identified on a pixel-by-pixel basis;
   reconstructing an image of an object scanned by the imaging device by interpolating the projection data corresponding to the conjugate pair of projection rays in accordance with:

$$\begin{cases} \frac{1-\Delta'}{1-\Delta'+\Delta} p(\gamma, \beta, i) + \frac{\Delta}{1-\Delta'+\Delta} p(-\gamma, \beta+\pi, i'+1), & \Delta \leq \Delta' \quad (1) \\ \frac{\Delta}{1-\Delta'+\Delta} p(\gamma, \beta, i+1) + \frac{1-\Delta'}{1-\Delta'+\Delta} p(-\gamma, \beta+\pi, i'), & \Delta > \Delta' \quad (2) \end{cases}$$

wherein q defines a detector row, $\gamma$ defines a detector angle, $\beta$ defines a projection angle, i and i' denote the integer part of q and q' and $\Delta$ and $\Delta'$ denote the fraction part of q and q'; and
   displaying the reconstructed image.

11. A method in accordance with claim 10 wherein the imaging device is a computed tomography imaging system and wherein the determining comprises identifying a source and detector position for the computed tomography imaging system corresponding to each of the projection rays.

12. A method in accordance with claim 10 wherein the conjugate pair are defined by projection rays spaced 180 degrees apart and having different tilt angles.

13. A method in accordance with claim 10 wherein the conjugate pair are defined by projection rays spaced 180 degrees apart and having a same tilt angle.

14. A method in accordance with claim 10 wherein the interpolating comprises determining an integer part and a fraction part of the projection data.

15. A computed tomography (CT) imaging device having a multi-row detector, said imaging device configured to:
   acquire projection data from a scan of an object;
   identify projection data corresponding to a conjugate pair of projection rays;
   determine an integer part and a fraction part for the projection data corresponding to each projection ray in the conjugate pair and for a source projection ray;
   interpolate the projection data corresponding to the conjugate pair of projection rays to reconstruct an image of the object being scanned based on a comparison of the fractional parts of the conjugate rays; and
   display the reconstructed image.

16. A CT imaging device in accordance with claim 15 further configured to perform a three-dimensional backprojection on the interpolated data to generate an image.

17. A CT imaging device in accordance with claim 15 wherein the interpolating comprises performing calculations in accordance with:

$$\begin{cases} \frac{1-\Delta'}{1-\Delta'+\Delta} p(\gamma, \beta, i) + \frac{\Delta}{1-\Delta'+\Delta} p(-\gamma, \beta+\pi, i'+1), & \Delta \leq \Delta' \quad (1) \\ \frac{\Delta}{1-\Delta'+\Delta} p(\gamma, \beta, i+1) + \frac{1-\Delta'}{1-\Delta'+\Delta} p(-\gamma, \beta+\pi, i'), & \Delta > \Delta' \quad (2) \end{cases}$$

wherein q defines a detector row, $\gamma$ defines a detector angle, $\beta$ defines a projection angle, i and i' denote the integer part of q and q' and $\Delta$ and $\Delta'$ denote the fraction part of q and q'.

* * * * *